United States Patent
Copeland

(10) Patent No.: US 11,771,722 B2
(45) Date of Patent: *Oct. 3, 2023

(54) METHODS FOR INHIBITING TUMOR GROWTH USING ANAEROBE MICROORGANISMS

(71) Applicant: Oxyrase, Inc., Mansfield, OH (US)

(72) Inventor: James C. Copeland, Mansfield, OH (US)

(73) Assignee: Oxyrase, Inc., Mansfiled, OH (US)

( * ) Notice: Subject to any disclaimer, the term of this patent is extended or adjusted under 35 U.S.C. 154(b) by 460 days.

This patent is subject to a terminal disclaimer.

(21) Appl. No.: 16/939,840

(22) Filed: Jul. 27, 2020

(65) Prior Publication Data

US 2020/0353017 A1 Nov. 12, 2020

Related U.S. Application Data

(63) Continuation of application No. 15/416,954, filed on Jan. 26, 2017, now Pat. No. 10,722,543.

(60) Provisional application No. 62/288,052, filed on Jan. 28, 2016.

(51) Int. Cl.
   *A61K 35/74* (2015.01)
   *A61K 47/10* (2017.01)
   *A61K 35/00* (2006.01)

(52) U.S. Cl.
   CPC .............. *A61K 35/74* (2013.01); *A61K 47/10* (2013.01); *A61K 2035/11* (2013.01)

(58) Field of Classification Search
   CPC ..... A61K 35/74; A61K 47/10; A61K 2035/11
   See application file for complete search history.

(56) References Cited

U.S. PATENT DOCUMENTS 10,076,556 B2 *  9/2018  Copeland ................ A61P 35/00
10,722,543 B2 *  7/2020  Copeland ................ A61K 9/10
11,207,386 B2 * 12/2021  Copeland ............... A61K 35/74

OTHER PUBLICATIONS

Strickley, "Solubilizing excipients in oral and injectable formulations", Pharm Res. Feb. 2004;21(2):201-30 (Year: 2004).*
Wikipedia, "*Escherichia coli*", https://en.wikipedia.org/wiki/Escherichia_coli (Year: 2022).*

* cited by examiner

*Primary Examiner* — Ruth A Davis
(74) *Attorney, Agent, or Firm* — Lippes Mathias LLP

(57) ABSTRACT

Methods of inhibiting or reducing tumor metabolism and growth are disclosed. A composition containing oxygen scavenging membrane fragments and anaerobe bacteria is injected into a tumor to interfere with tumor growth and metabolism, leading to tumor necrosis. The composition may also contain a cryoprotectant, which permits the composition to be stored at sub-zero temperatures without freezing.

16 Claims, 8 Drawing Sheets

METHODS FOR INHIBITING TUMOR GROWTH USING ANAEROBE MICROORGANISMS

CROSS-REFERENCE TO RELATED APPLICATIONS

This application is a continuation of U.S. patent application Ser. No. 15/416,954, filed Jan. 26, 2017, now U.S. Pat. No. 10,722,543, which claims priority to U.S. Provisional Patent Application Ser. No. 62/288,052, filed Jan. 28, 2016. The disclosures of these applications are hereby fully incorporated by reference herein.

BACKGROUND

The present disclosure relates to methods for inhibiting or reducing cancerous tumor metabolism, growth, and proliferation. Compositions for use in such methods are also disclosed.

Cancer is the abnormal growth of cells, which can create masses of tissue that can become malignant tumors or neoplasms. These formations can invade and destroy surrounding tissues, and may spread to other parts of the body (metastasis).

Physicians are constantly seeking new forms of cancer treatment to either bolster the effects of or supplant current cancer treatments such as chemotherapy, immunotherapy, radiation therapy, drug therapy, and cell transplantation. Alone, many of these treatments require repeated administrations with no guarantee of a reduction in tumor cell growth and proliferation. Further, many of these treatments result in adverse side effects, requiring subjects to undergo further discomfort and therapies.

Tumors require oxygen in order to grow. Often tumors grow faster than their oxygen supplies can support. This results in hypoxic regions within the tumors. Hypoxic regions can support infection with anaerobe microorganisms, and tumor infection by an anaerobe can lead to the tumor's demise.

It would be desirable to identify additional compositions and methods that can be used to deliver anaerobes effectively to a patient.

BRIEF DESCRIPTION

Disclosed in various embodiments herein are methods for inhibiting cancerous tumor metabolism, growth, and/or proliferation, both in vitro and in vivo. Generally speaking, a pharmaceutical/therapeutic composition comprising oxygen reducing membrane fragments and anaerobe microorganisms is administered intratumorally. It is believed that the membrane fragments under certain conditions create an anaerobic environment within the tumor, inhibiting growth or resulting in cell death. Because it affects a fundamental attribute of the tumor, i.e. the metabolic need for oxygen, this inhibition and treatment process should impact all types of tumors. The impact may also be dose-dependent. In addition, the anoxic environment in tumors makes them reliably "hospitable" to anaerobe infection. The pharmaceutical/therapeutic composition may also include a cryoprotectant to enable the formation of a product that has long term storage ability and can be injected into a tumor to cause infection and demise of the tumor.

In one aspect, the present disclosure is directed to pharmaceutical/therapeutic compositions, and methods of utilizing the same, for inhibiting cancerous tumor metabolism growth and/or proliferation. The pharmaceutical/therapeutic compositions contain a cryoprotectant, oxygen scavenging membrane fragments, and at least one anaerobe microorganism. The suspension is then maintained at sub-zero temperatures. The composition can then be used to reduce dissolved oxygen in vitro from a body or mass containing cancerous tumor cells.

In another aspect, the present disclosure relates to methods for treating a cancerous tumor, comprising intratumorally administering to a patient, including a human or other mammal, a therapeutic composition comprising a pharmaceutically effective amount of oxygen scavenging membrane fragments and a pharmaceutically effective amount of anaerobe microorganisms.

The oxygen scavenging membrane fragments can be derived from the cytoplasmic membranes of *Escherichia coli*, *Salmonella typhimurium*, *Gluconobacter oxydans*, *Pseudomonas aeruginosa*, or *Acetobacter*. In particular embodiments, the oxygen scavenging membrane fragments are derived from *Escherichia coli*.

The composition can further comprise a hydrogen donating substance. In particular embodiments, the hydrogen donating substance is lactic acid, succinic acid, alpha-glycerol phosphate, formic acid, malic acid, or a salt thereof. The hydrogen donating substance may be present in the amount of about 1 wt % to about 5 wt % of the composition.

The composition may be in the form of an injection, solution, suspension, or emulsion. The composition may contain the oxygen scavenging membrane fragments in an amount of about 0.01 units per milliliter to about 100 units per milliliter (u/mL), or greater than 0.01 u/mL, or greater than 0.5 u/mL, or greater than 1 u/mL, or an amount from 1 u/mL to 10 u/mL, or from 5 u/mL to 10 u/mL.

The cancerous tumors treated by these methods can be breast, brain, cervical, colon, liver, lung, ovarian, pancreatic, prostate, or bone cancer tumors.

The compositions can be administered in combination with chemotherapy, immunotherapy, radiation therapy, drug therapy, or cell transplantation.

Desirably, the administration of the composition creates localized hypoxia and fosters replication of anaerobes.

It is particularly contemplated that the oxygen scavenging membrane fragments and the anaerobe bacteria are stored in a liquid state at sub-zero temperatures to increase their usable lifetime as a pharmaceutical/treatment. The cryoprotectant may be any compound that decreases the freezing point of water, thereby preventing ice formation or damage. The composition may contain glycerol or polyethylene glycol as a cryoprotectant. The composition may contain the cryoprotectant in an amount of about 15% by weight to about 65% by weight, or from about 50 wt % to about 65 wt %.

This permits the composition to be stored at a temperature below 0° C. but greater than −70° C. (i.e. liquid nitrogen does not need to be used for storage). The storage temperature should be one where the composition remains in a liquid state, which can depend upon the concentration of the cryoprotectant. In particular embodiments, the composition is stored within a temperature range of about −25° C. to about −5° C. This composition can be stored in self-defrosting freezers, significantly reducing complexity and cost.

In some particular embodiments, when the composition containing the suspended anaerobes is placed in a container, a layer of oil is then overlaid on the composition. This can aid in stabilizing the sample, by blocking air from dissolving into the underlying composition and harming the anaerobe microorganism.

These and other non-limiting characteristics of the disclosure are more particularly disclosed below.

DETAILED DESCRIPTION

Figure 1:
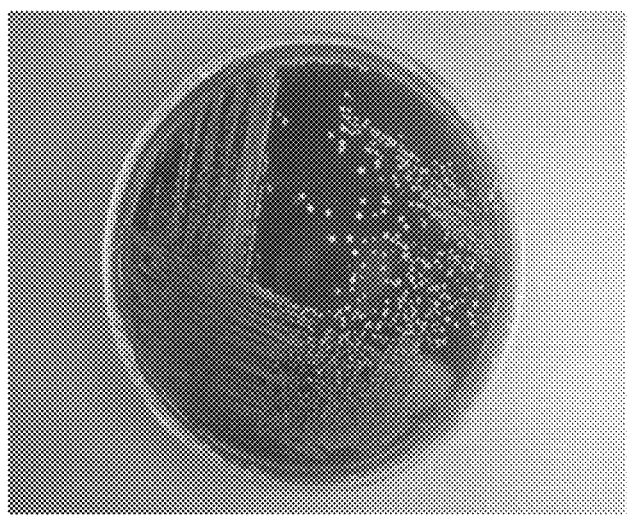
FIG. 1 is a set of images showing an example of a plate plated with the quadrant streak method as well as the plating scheme.
Figure 1:
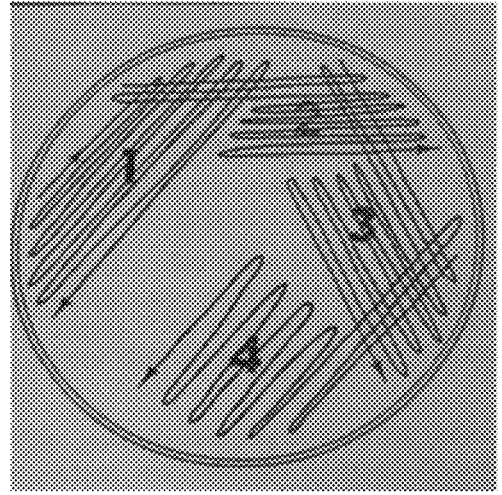

The present disclosure may be understood more readily by reference to the following detailed description of desired embodiments and the examples included therein. In the following specification and the claims which follow, reference will be made to a number of terms which will be defined to have the following meanings.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

"Oxyrase®" is a commercially available enzyme system (from Oxyrase, Inc.) obtained from the cytoplasmic membranes of *Escherichia coli* to produce anaerobic conditions in a wide variety of environments. The system is available in the form of membrane fragments that scavenge oxygen.

The term "unit" is used herein to refer to a given amount of membrane fragments. One unit is defined as the amount of oxygen scavenging membrane fragments that will reduce dissolved oxygen in one milliliter of air saturated 40 mM phosphate buffer, pH 8.4, at 37 degrees Celsius, at the rate of 1% per second.

The term "cryoprotectant" is used herein to refer to a substance used to protect biological tissue from freezing damage. Examples of cryoprotectants include ethylene glycol, propylene glycol, glycerol, and polyethylene glycol, and dimethyl sulfoxide (DMSO).

The term "polyethylene glycol" is used herein to refer to compounds of the formula $H-(OCH_2CH_2)_n-OH$, where n can be any number from 1 to about 35,000. It is noted though that typical values range from 1 to about 800. It is also noted that in commercially available formulations, the glycols are distributed in a statistical fashion similar to polymers, and the weight-average value of n.

The present application relates to methods for treating cancerous tumors using pharmaceutical/therapeutic compositions comprising oxygen scavenging membrane fragments and anaerobe microorganisms. In this regard, the oxygen scavenging membranes remove oxygen from in vivo and/or in vitro environments, thereby creating environments for anaerobic colonization within tumors, with the goal of causing tumor necrosis.

The pharmaceutical/therapeutic compositions can also include, if desired, a hydrogen donating substance. The compositions can also include cryoprotectants. When the anaerobe microorganisms in the composition are subsequently maintained at sub-zero temperatures, the anaerobes remain viable for a prolonged period of time. The oxygen-deprived environments, in addition to the cryoprotectants, protect cells and tissues from damage during storage, particularly those that require anaerobic conditions, by preventing ice formation and potential chemical reactions. These anaerobes can be preserved in a vegetative state for long time periods, increasing the usable lifetime of the pharmaceutical compositions.

The present disclosure removes oxygen through the use of oxygen scavenging membrane fragments. The membrane fragments, which contain an electron transport system that reduces oxygen to water, may be obtained from various sources. It is known that a great number of bacteria have cytoplasmic membranes which contain the electron transport system that effectively reduces oxygen to water if a suitable hydrogen donor is present in the medium. Some suitable bacterial sources include *Escherichia coli, Salmonella typhimurium, Gluconobacter oxydans, Pseudomonas aeruginosa*, and *Acetobacter*. These bacterial membranes have been highly effective in removing oxygen from media and other aqueous and semi-solid environments.

The same oxygen reducing effects produced by the cell membrane fragments from the bacteria sources indicated above can also be obtained by the use of oxygen reducing membranes from, for example, the mitochondrial organelles of a large number of higher non-bacteria organisms. More particularly, a great number of fungi, yeasts, plants, and animals have mitochondria that reduce oxygen to water if a suitable hydrogen donor is present in the medium. Some of the sources of oxygen reducing membranes from these mitochondria are: beef heart muscle, potato tuber, spinach, *Saccharomyces, Neurospora, Aspergillus, Euglena*, and *Chlamydomonas*. Of all microbes, anaerobes are among the most difficult to isolate, grow, and preserve. Therefore, any damage due to freezing only exacerbates the issue of recovering representative cells from the storage population.

Oxygen scavenging fragments are commercially available as Oxyrase®. Oxyrase® oxygen scavenging membrane fragments consist of an enzyme system derived from the cytoplasmic membranes of microorganisms. Sterile (EC) and nonsterile (EC/NS) Oxyrase® oxygen scavenging membrane fragments in particular are derived from the cell membrane fragments of *E. coli* (0.2 microns or smaller) suspended in 20 mM phosphate buffer at a neutral pH. Substrates for Oxyrase® oxygen scavenging membrane fragments include lactic acid, succinic acid, formic acid, or their salts, and alpha-glycerol phosphate in addition to oxygen. One unit/ml Oxyrase® activity will reduce dissolved oxygen (air saturated 40 mM phosphate buffer, pH 8.4, at 37 degrees Celsius) at the rate of 1% per second. The rate of oxygen removal increases with temperature, and above 55 degrees Celsius, Oxyrase® oxygen scavenging membrane fragments begin to be inactivated but will persist up to 80 degrees Celsius. Oxyrase® oxygen scavenging membrane fragments are active over a wide pH range of 6.8 to 8.4.

The exact amount of membranes containing the enzyme systems needed to reduce oxygen in the tumor can vary by a number of parameters including pH, temperature, kinds and amounts of substrate present, and amount of oxygen present within the tumor. Some experimentation may be necessary to optimize the effectiveness of the membranes on the various types of tumors. In some embodiments, the pharmaceutical composition contains the oxygen scavenging membrane fragments in the amount of about 0.01 units/mL to about 100 units/mL, or from about 0.01 units/mL to about 10 units/mL, or from about 0.3 unit/mL to about 10 units/mL, or from about 1 unit/mL to about 10 units/m L.

The use of Oxyrase® oxygen scavenging membrane fragments is believed to aid in reducing tumor growth. By starving aerobic cells of oxygen, Oxyrase® oxygen scavenging membrane fragments place cells in a metabolic resting state, thereby precluding cell growth and replication. Further, the removal of oxygen from the environment also aids in the survival of anaerobe cells which can cause tumor necrosis.

The pharmaceutical/therapeutic composition also includes at least one anaerobe bacteria species. A mix of anaerobe bacteria may be included in the pharmaceutical composition or administered in tandem with said pharmaceutical composition. The anaerobe bacteria species may be *Bacteroides fragilis, Bifidobacterium adolescentis, Clostridium perfringens, Fusobacterium nucleatum, Porphyromonas levii, Peptostreptococcus anaerobius*, or *Prevotella melaninogenica*, for example. The anaerobe bacteria can be present in the amount of about $1 \times 10^6$ to about $1 \times 10^8$ colony-forming units (CFU) per milliliter of the composition. The anaerobe bacteria may be present in the composition in any form, for example as spores or as cells.

A hydrogen donating substance (i.e., an organic substrate) may be necessary in order for the membrane fragments to perform their oxygen removing functions. Suitable hydrogen donors are lactic acid, succinic acid, alpha-glycerol phosphate, formic acid, malic acid, and where available, their corresponding salts. The hydrogen donating substance may be present in the composition in the amount of about 1 wt % to about 5 wt %.

Cryoprotectants are substances used to protect biological tissue from freezing damage. In order to preserve cells and tissues, cryoprotectants must be non-toxic to the cells. Typical cryoprotectants include glycerol, dimethyl sulfoxide (DMSO), and glycols, including ethylene glycol, propylene glycol, polyethylene glycol, and glycerol.

Higher concentrations of cryoprotectants ("high" meaning greater than 15 wt %) can be used to preserve anaerobes and have resulted in unexpected advantages. Namely higher concentrations of cryoprotectants prevent the formation of ice crystals, thereby precluding the freezing of cells and the damage and/or killing of preserved cells. This results in higher numbers of cells being recovered after storage at sub-zero temperatures. It has been found that cells stored at below zero degrees Celsius are still viable after over twelve (12) months or more of storage.

In some embodiments, the composition comprises glycerol. Glycerol is a small molecule that can pass through the semipermeable membrane of cells and gain entry into their interior. The cryoprotectant nature of glycerol is available both inside and outside the cell. Glycerol forms strong hydrogen bonds with water molecules, thereby disrupting the crystal lattice formation of ice and maintaining the liquid nature of the composition.

In some other embodiments, the composition comprises polyethylene glycol (PEG). Polyethylene glycol is a cryoprotectant that is impermeable to cell membranes and can be made at different molecular weights. Its mode of action is limited to the space "outside" a cell. While porins (i.e. channels within a cell membrane) allow movement of small hydrophilic molecules between the interior of a cell and the exterior of a cell, large hydrophilic molecules, such as polyethylene glycol, are too large to pass through the porins. In particular embodiments, the polyethylene glycol has about 400 glycol moieties (designated as PEG 400).

The composition may contain one or more cryoprotectants in the amount of about 15% to about 65% by weight, or from about 50 wt % to about 65 wt %. This lowers the freezing point of the composition. For example, if 53 wt % of glycerol is used, the freezing temperature of the composition is decreased to −26° C.

The composition also contains water as a solvent for the various ingredients. Desirably, the composition is isotonic. In embodiments, the composition has an osmolality of about 280 milliOsmoles/liter (mOsm/L) to about 300 mOsm/L.

In this regard, it is contemplated that the effective lifetime of the pharmaceutical composition containing the oxygen scavenging membrane fragments and the anaerobe bacteria can be extended by storage at sub-zero temperatures. The composition can thus be stored in a self-defrosting freezer under these conditions. In such freezers, the temperature cycles up and down within a temperature range. For example, the temperature is brought up from −25° C. to −17° C. for about an hour, then reduced to the lower temperature. This cycle can occur at about 24-hour intervals. Such freezers are significantly cheaper compared to cryogenic freezers. It is noted that the composition remains in a liquid state at these sub-zero temperatures, so that there is reduced damage/death to the anaerobes that are suspended in the composition.

In practical use, after the pharmaceutical compositions are warmed to reach room temperature, they are administered intratumorally to a patient, including a human or other mammal. Thus, it should be noted that the cryoprotectant should be non-toxic to mammals (e.g. humans) at low absolute dosages.

It is contemplated that the pharmaceutical compositions will be injected into the tumor. The dose used in a particular formulation or application will be determined by the requirements of the particular disease state and other constraints.

It is also contemplated that prior to injection of the pharmaceutical composition containing the anaerobe bacteria into the tumor, that the tumor could be prepared by first injecting a priming composition that includes oxygen scavenging membrane fragments but does not include anaerobe bacteria. The priming composition would create an anoxic environment within the tumor that otherwise might not exist. The pharmaceutical composition (containing anaerobe bacteria) is subsequently injected into the anoxic environment within the tumor, to infect the tumor with the anaerobe bacteria.

If desired, the pharmaceutical composition may also include other excipients. Particular excipients can include buffering agents, polymers, and stabilizers, which may be useful. Buffering agents are used to control the pH of the composition. Polymers with nonpolar moieties such as polyethylene glycol can also be used as surfactants. Protein stabilizers can include polyols, sugars, amino acids, amines, and salts. Suitable sugars include sucrose and trehalose. Amino acids include histidine, arginine, glycine, methionine, proline, lysine, glutamic acid, and mixtures thereof. It should be noted that particular molecules can serve multiple purposes. For example, histidine can act as a buffering agent and an antioxidant.

Dose will depend on a variety of factors, including disease type, patient age, patient weight, and tolerance. The dose of a particular patient can be determined by the skilled clinician using standard pharmacological approaches in view of the above factors. The response to treatment may be monitored by conventional means. The skilled clinician will adjust the dose based on the response to treatment revealed by these measurements. A single administration may usually be sufficient to produce a therapeutic effect, but it is contemplated that multiple administrations will be used to assure continued response over a substantial period of time. Because the pharmaceutical composition is injected intratumorally, it is believed that they will have a long half-life in the body, so that the composition may only need to be administered once or twice a month, or possibly once a week.

The pharmaceutical compositions can be used to treat various types of tumors, including a breast, cervical, colon, liver, lung, ovarian, pancreatic, prostate, brain, or bone cancer tumors. The term "treat" is used to refer to a reduction in progression of the disease, or a regression in the disease. This can be measured by conventional methods, such as a reduction in tumor size, or other accepted means.

The present disclosure is further illustrated in the following non-limiting working examples, it being understood that these examples are intended to be illustrative only and that the disclosure is not intended to be limited to the materials, conditions, process parameters and the like recited herein.

EXAMPLES

The following examples both employ the quadrant streak method to determine the efficacy of Oxyrase® oxygen scavenging membrane fragments in suspensions for preserving and storing biological material. The method consists of streaking the most concentrated inoculum (1 loop-full) onto a restricted area on the surface of a plate (about one-fourth the surface area). The plate is then rotated about 90 degrees in a counter-clockwise direction, and a second quadrant is cross-streaked to overlap the first quadrant. This is done in turn for a third and fourth quadrant as shown in FIG. 1. After incubation, the densest quadrant is the first quadrant and subsequent quadrants have fewer colonies. The furthest quadrant that has well isolated colonies determines the score of the plate. For example, FIG. 1 contains an image of a plate with a score of 4, as the fourth quadrant was the furthest quadrant on the plate with well isolated colonies. Further resolution is designated by adding a + or − to the score (e.g., 4+ or 4−). A + represents a heavily colonized quadrant and a − represents a thinly colonized quadrant. This technique provides a semi-quantitative method to determine cell density in the sample and is reliable when comparisons are made for the same individual.

First Set of Experiments

Materials and Methods

Glycerol was used as the cryoprotectant. 266 mL 20 mM phosphate buffer (pH 7.5), 52 mL DL lactic acid (60% syrup (w/w)), 100 grams succinic acid (disodium salt hexahydrate), 0.41 grams cysteine, 66 grams trehalose, and 518 mL glycerol were combined and dissolved. The pH was adjusted with 50% weight by weight sodium hydroxide to a pH of 7.6+/−0.1 at 15 to 20 degrees Celsius. The solution was then sterilized by autoclaving at 121 degrees Celsius for 15 to 20 minutes. After the sterile mixture cooled, Oxyrase® oxygen scavenging membrane fragments were added to a final activity of 30 u/mL and gently mixed. The mixture was then aseptically distributed in volumes of 5.0 mL into sterile, screw-cap scintillation vials. Five vials were tested for sterility at 37 degrees Celsius for seven days. Vials containing the liquid mixture were then stored at −20 degrees Celsius.

For use, the frozen single vial was pre-warmed to room temperature. A heavy suspension of cells was created from a PRAS Brucella plate or a Schaedler OxyPlate from the confluent quadrant of a quadrant streaked plate in 1 mL of sterile 20 mM phosphate buffer (pH 7.6). The cell suspension was then aseptically transferred to the pre-warmed vial and gently mixed to disperse. The vial was then incubated at 37 degrees Celsius for 30 minutes before placing the vial containing the suspension into a freezer at −20 degrees Celsius. After seven days, one loop of mixed suspension was aseptically taken from the vial and an appropriate plate was quadrant streaked. The plate was then incubated at 37 degrees Celsius and observed at 24 hours, 48 hours, and 72 hours.

Suspensions containing Oxyrase® oxygen scavenging membrane fragments and microbes were prepared. Particularly, suspensions were prepared for *B. fragilis, C. perfringens, F. nucleatum, P. levii, P. anaerobius, B. adolescentis, P. melaninogenica, S. aureus, P. mirabilis*, and *E. coli*. At specified monthly intervals over the course of a year, a loopful of suspension was aseptically removed from the storage vial and was quadrant streaked on a PRAS *Brucella* plate. Plates containing anaerobes were incubated at 37 degrees Celsius in an anaerobic jar with a catalyst to remove oxygen and observed at an appropriate time.

Some months later, two additional Oxyrase® suspensions were created. One suspension contained *F. nucleatum* with oil while the other suspension contained *P. melaninogenica* with oil.

Figure 2:
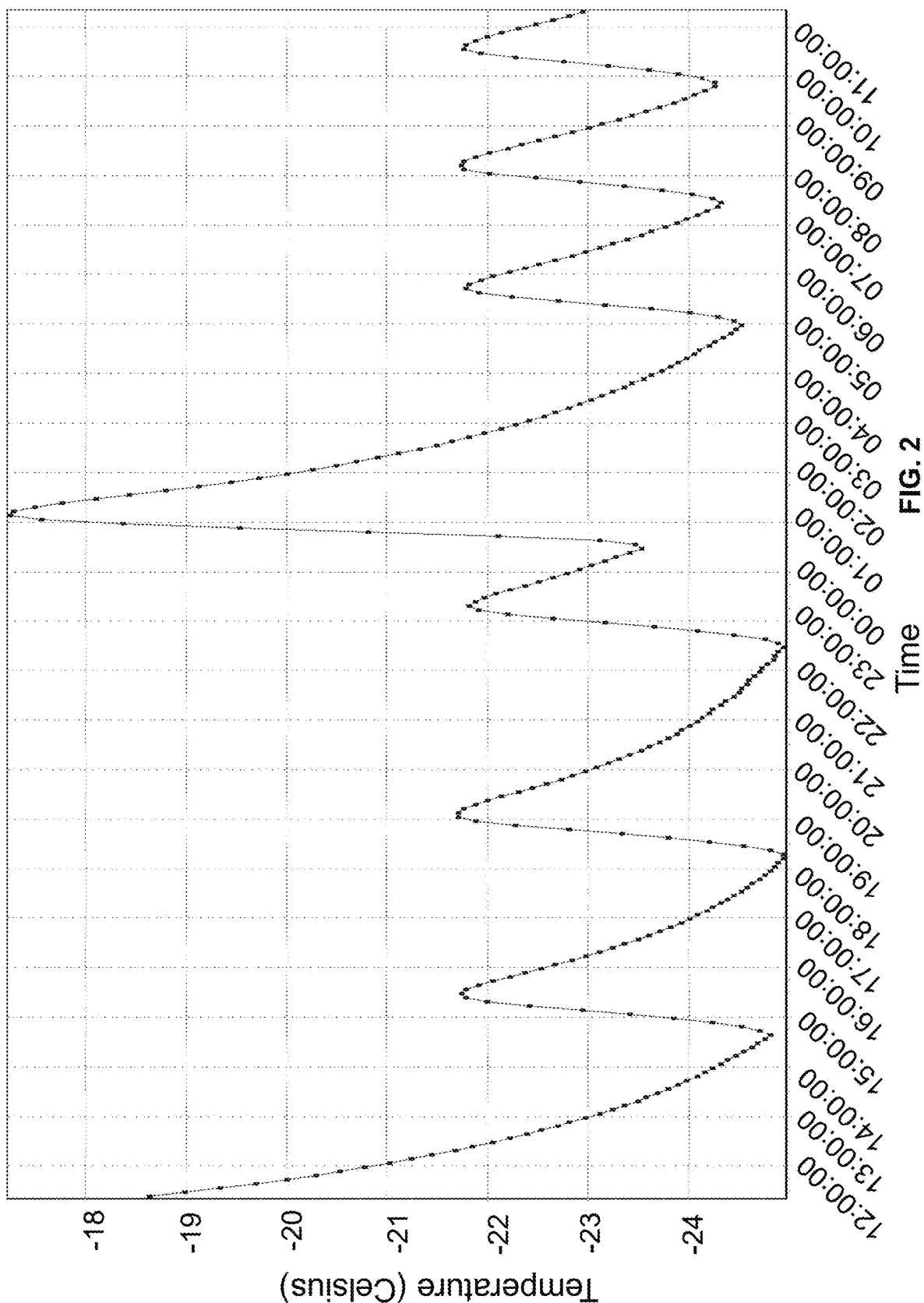
FIG. 2 is a graph indicating the temperature cycle of the self-defrosting freezer holding the stored suspensions containing Oxyrase® oxygen scavenging membrane fragments and the test microbes.

The microbes stored in the Oxyrase® suspension were stored in a self-defrosting freezer, which meant the temperature was brought to −17 degrees Celsius and then returned to −20 degrees Celsius or below. The freezer cycled about every 24 hours. As shown in FIG. 2, the temperatures ranged over a high of −17 degrees Celsius to a low of −25 degrees Celsius.

Results

Tables 1-3 below express the results of the monthly quadrant streak tests for the microbes in suspension with Oxyrase® oxygen scavenging membrane fragments and Glycerol Base. They are reported by the month of sampling. In some assays, the colony counts were limited to the first quadrant and had few colonies (less than a 1−). These were counted and listed as colony-forming units (cfu).

TABLE 1

Recovery of Microbes Stored in Glycerol Base with Oxyrase ® oxygen scavenging membrane fragments at −20 Degrees Celsius for 5 months
Set A

| Initial Score | Microbe | 1 month | 2 months | 3 months | 4 months | 5 months |
|---|---|---|---|---|---|---|
| 4+ | B. fragilis | 4 | 4 | 4 | 4+ | 4 |
| 3+ | C. perfringens | 3− | 2+ | 2+ | 3+ | 2+ |
| 3+ | F. nucleatum | 3− | 2 | 2+ | 1+ | 3− |
|  | F. nucleatum with oil |  |  |  | 4 | 2+ |
| 3+ | P. levii | 4 | 4− | 3+ | 3+ | 3+ |
| 4+ | P. anaerobius | 3+ | 3+ | 3+ | 4 | 3 |
| 4 | B. adolescentis | 3+ | 4− | 3− | 3− | 3 |
| 3 | P. melaninogenica | 3+ | 2+ | 2+ | 1+ | 2+ |
|  | P. melaninogenica with oil |  |  |  | 4 | 2+ |
| 4− | S. aureus | 4− | 4+ | 4+ | 4 | 4 |
| 4 | P. mirabilis | 4− | 4− | 4+ | 4− | 4+ |
| 4 | E. coli | 4 | 4− | 4− | 4 | 4 |

TABLE 2

Recovery of Microbes Stored in Glycerol Base with Oxyrase ® oxygen scavenging membrane fragments at −20 Degrees Celsius for 10 months.
Set B

| Initial Score | Microbe | 6 month | 7 month | 8 month | 9 month | 10 month |
|---|---|---|---|---|---|---|
| 4+ | B. fragilis | 4+ | 4 | 4− | 3+ | 3+ |
| 3+ | C. perfringens | 3− | 3− | 3− | 3 | 3 |

TABLE 2-continued

Recovery of Microbes Stored in Glycerol Base with Oxyrase ®
oxygen scavenging membrane fragments at −20 Degrees Celsius for 10 months.
Set B

| Initial Score | Microbe | Time Stored | | | | |
|---|---|---|---|---|---|---|
| | | 6 month | 7 month | 8 month | 9 month | 10 month |
| 3+ | F. nucleatum | NG/2 cfu | 2 cfu/2 | NG | NG/1+ | NG/2− |
| | F. nucleatum with oil | 2 | 2 | 1+ | 1+ | 2− |
| 3+ | P. levii | 3+ | 4 | 3+ | 3 | 3− |
| 4+ | P. anaerobius | 3+ | 4 | 3+ | 3+ | 2+ |
| 4 | B. adolescentis | 3+ | 3 | 3− | 3− | 3+ |
| 3 | P. melaninogenica | NG/2+ | 6cfu/2+ | 1+ | NG/2+ | 1+ |
| | P. melaninogenica with oil | 2+ | 3+ | 1+ | 1 | 2− |
| 4− | S. aureus | 4+ | 4+ | 4+ | 4+ | 4 |
| 4 | P. mirabilis | 4+ | 4+ | 4 | 3+ | 4 |
| 4 | E. coli | 3+ | 3+ | 4− | 3+ | 4 |

TABLE 3

Recovery of Microbes Stored in Glycerol Base with Oxyrase ®
oxygen scavenging membrane fragments at −20 Degrees Celsius
for 15 MonthsSet C

| Initial Score | Microbe | Time Stored | | |
|---|---|---|---|---|
| | | 11 month | 12 month | 15 month |
| 4+ | B. fragilis | 3+ | 4 | 3+ |
| 3+ | C. perfringens | 3+ | 3− | 3 |
| 3+ | F. nucleatum | 1+ | 2cfu/2 | NG/1+ |
| | F. nucleatum with oil | 2− | 2− | 2− |
| 3+ | P. levii | 2+ | 4 | 3 |
| 4+ | P. anaerobius | 2+ | 4 | 3+ |
| 4 | B. adolescentis | 1+ | 3 | 3− |
| 3 | P. melaninogenica | NG/2+ | 6cfu/2+ | NG/2+ |
| | P. melaninogenica with oil | 2− | 2− | 2− |
| 4− | S. aureus | 4 | 4+ | 4+ |
| 4 | P. mirabilis | 4 | 4+ | 3+ |
| 4 | E. coli | 4 | 3+ | 3+ |

With respect to Tables 1-3, several values are noted as "NG," which are indicative of "no growth." NG/2+ denotes that after a first determination, there was no growth, but after a second determination, growth was scored at 2+. In such a case, the second determination was made as the first determination led to a suspect first result. Also with respect to Tables 1-3, 2 cfu/2 denotes that after a first determination, two colony forming units (cfu) were observed, and after a second determination, growth was scored at 2.

As shown, suspensions containing Oxyrase® oxygen scavenging membrane fragments exhibited consistent recovery scores over the course of at least fifteen months. The only exceptions were F. nucleatum, P. levii, and P. melaninogenica, which are difficult microbes to suspend uniformly.

The recovered cells remained undamaged as the cells and medium did not freeze during preparation and storage.

Second Set of Experiments

Materials and Methods

Polyethylene glycol was used as the cryoprotectant. 266 mL 20 mM phosphate buffer (pH 7.5), 52 mL DL lactic acid (60% syrup (w/w)), 100 grams succinic acid (disodium salt hexahydrate), 0.41 grams cysteine, 66 grams trehalose, and 518 mL polyethylene glycol (PEG 400) were combined and dissolved. The pH was adjusted with 50% weight by weight sodium hydroxide to a pH of 7.6+/−0.1 at 15 to 20 degrees Celsius. The solution was then sterilized by autoclaving at 121 degrees Celsius for 15 to 20 minutes. After the sterile mixture cooled, Oxyrase® oxygen scavenging membrane fragments were added to a final activity of 30 u/mL and gently mixed. The mixture was then aseptically distributed in volumes of 5.0 mL into sterile, screw-cap scintillation vials. Five vials were tested for sterility at 37 degrees Celsius for seven days. Vials containing the liquid mixture were then stored at −20 degrees Celsius.

For use, the frozen single vial was pre-warmed to room temperature. A heavy suspension of cells was created from a PRAS Brucella plate or a Schaedler OxyPlate from the confluent quadrant of a quadrant streaked plate in 1 mL of sterile 20 mM phosphate buffer (pH 7.6). The cell suspension was then aseptically transferred to the pre-warmed vial and gently mixed to disperse. The vial was then incubated at 37 degrees Celsius for 30 minutes before placing the vial containing the suspension into a freezer at −20 degrees Celsius. After seven days, one loop of mixed suspension was aseptically taken from the vial and an appropriate plate was quadrant streaked. The plate was then incubated at 37 degrees Celsius and observed at 24 hours, 48 hours, and 72 hours.

Suspensions containing Oxyrase® oxygen scavenging membrane fragments and microbes were prepared. Particularly, suspensions were prepared for B. fragilis, C. perfringens, F. nucleatum, P. levii, P. anaerobius, B. adolescentis, P. melaninogenica, S. aureus, P. mirabilis, and E. coli. At specified monthly intervals over the course of eight months, a loopful of suspension was aseptically removed from the storage vial and was quadrant streaked on a PRAS Brucella plate. Plates containing anaerobes were incubated at 37 degrees Celsius in an anaerobic jar with a catalyst to remove oxygen and observed at an appropriate time.

The microbes stored in the Oxyrase® suspension were stored in a self-defrosting freezer, which cycled about every 24 hours. As shown in FIG. 2, the temperatures ranged over a high of −17 degrees Celsius to a low of −25 degrees Celsius. In addition, there were smaller cycles from −25 degrees Celsius to −22 degrees Celsius over a 3-hour period. It is noted that the temperature ranges for the freezer refer to the ambient temperature inside the freezer. The walls of the freezer may be at a different temperature (e.g. to affect defrosting), and the temperature of items inside the freezer may also be different.

Results

Table 4 below expresses the results of the monthly quadrant streak tests for the microbes in suspension with Oxyrase® oxygen scavenging membrane fragments and Polyethylene Glycol.

TABLE 4

Recovery of Microbes Stored in PEG Base with Oxyrase ® oxygen scavenging membrane fragments up to 8 Months at −20 Degrees Celsius.

| Initial Score | Microbe | \multicolumn{8}{c}{Time Stored (Months)} | | | | | | | |
|---|---|---|---|---|---|---|---|---|---|
| | | 1 | 2 | 3 | 4 | 5 | 6 | 7 | 8 |
| 4 | B. fragilis | 4 | 4− | 4+ | 4 | 4 | 4 | — | 2 |
| 2+ | C. perfringens | 3− | 3+ | 4 | 3 | 3+ | 3 | — | 3 |
| 2 | F. nucleatum | 1+ | 2+ | 2 | 2 | 2 | 2 | — | NG |
| 2 | P. levii | 4+ | 4+ | 4 | 4 | 4 | 3+ | — | 3 |
| 3− | P. anaerobius | 4− | 4− | 4 | 4− | 4− | 4 | — | 2+ |
| 3 | B. adolescentis | 3+ | 4 | 4 | 4 | 4 | 4 | — | 4− |
| 1+ | P. melaninogenica | 2 | 2+ | 3 | 2 | 2 | 2− | — | NG |
| 4 | S. aureus | 4 | 4 | 4+ | 4 | 4 | 4 | — | 4 |
| 3+ | P. mirabilis | 4 | 4 | 4 | 4 | 4 | 4 | — | 4+ |
| 3+ | E. coli | 3+ | 4 | 4 | 3+ | 3+ | 3+ | — | 3+ |

Like the results of the first experiment, the results of the second experiment indicate suspensions containing Oxyrase® oxygen scavenging membrane fragments lead to higher and more consistent recovery rates of stored biological specimens. The ratios of recovered cells to initial cells were very high, often greater than 75% of the initial value.

Sampling issues are again apparent throughout the table, particularly with respect to the challenging anaerobes F. nucleatum and P. melaninogenica. There is no indication that viability dropped as time of storage increased.

Third Set of Experiments

An additional set of experiments was conducted to compare the actions of anaerobe infection alone with anaerobe infection with Oxyrase® oxygen scavenging membrane fragments and substrate on tumor growth.

Materials and Methods

Eighteen (18) female BALB/C mice were purchased from Charles River Laboratories at four (4) weeks old. In addition, eighteen C57BL/6 mice were purchased from Charles River Laboratories at four (4) weeks old. The animals were fed ad libitum Teklad Certified Global 18% Protein Rodent diet (2018C). The mice were housed in plastic shoebox cages with bedding and kept in a 12-hour light cycle at 20-26 degrees Celsius (68-78.8 degrees Fahrenheit) and 30-70% humidity.

4T1 murine breast cancer cells and Lewis lung carcinoma (LLC) cancer cell lines were obtained from American Type Culture Collection (ATCC, Manassas, Va.). 4T1 is an animal model for stage IV human breast cancer. The LLC cells were cultured in ATCC-formulated Dulbecco's Modified Eagle's Medium, containing 10% fetal bovine serum (FBS) and 1% of 100× Penicillin-streptomycin glutamine, while the 4T1 cells were cultured in RPMI-1649 medium containing 10% FBS and 1% of 100× Penicillin-streptomycin glutamine. Cells were cultured in a humidified incubator at 37 degrees Celsius in an appropriate atmosphere of 5% $CO_2$ and 95% air.

Tumor cells in passage four were used for the implantation and were harvested during log phase growth. BALB/c mice were inoculated with $1\times10^6$ 4T1 cells on their right flanks. C57/CL mice were inoculated with $1\times10^6$ LLC cells on their right flanks. Tumor measurements were initiated as soon as the tumors were palpable.

Thereafter, tumors were measured twice weekly. Tumors were measured in two dimensions using calipers and volume was calculated using the formula:

$$\text{Tumor volume (mm}^3) = \frac{\text{width}^2 \times \text{length}}{2}$$

where width and length are dimensions of a tumor in mm. Tumor weight may be estimated with the assumption 1 mg is equivalent to 1 mm³ or tumor volume.

Animals were randomized using the stratified random sampling algorithm when tumors reached a size range of 74.9-279.5 mm³ for the 4T1 model or 107.5-257.4 mm³ for the LLC model. Treatments or control vehicle (PBS) were administered on Day 1 following randomization.

The following concentrations were provided by the sponsor:

C. perfringens

C. perfringens was cultured for 18-24 hours with about $7\times10^8$ cfu/mL to be used at 1:100 dilution. With respect to the substrate, 4 M sodium L-lactate was used at 1:100 dilution (final concentration 40 mM). 110 u/ml Oxyrase® oxygen scavenging membrane fragments were used at a final concentration of 20 u/mL.

*B. adolescentis*

BHI-OB was cultured for 18-24 hours with about $7\times10^8$ cfu/mL to be used at 1:100 dilution. With respect to the substrate, 4 M sodium L-lactate was used at 1:100 dilution (final concentration 40 mM). 110 u/ml Oxyrase® oxygen scavenging membrane fragments were used at a final concentration of 20 u/mL.

In order to achieve the correct concentrations, materials were prepared as follows:

Schaedler-Blood Agar Oxyplates were removed from the refrigerator and allowed to reach room temperature. The oxyplates, with the lids removed, were then placed in a Class II biological safety cabinet (BSC) to eliminate condensation. PBS, substrate, and Oxyrase® oxygen scavenging membrane fragments were placed in the Class II BSC. *B. adolescentis* and *C. perfringens* were removed from the incubator and placed in the Class II BSC.

With respect to treatment Group 1, 9 mL control PBS was slowly loaded by pipette into a dosing vial and cap with crimper.

Regarding treatment Group 2 (*C. perfringens* alone), 8.71 mL PBS was slowly loaded by pipette into a dosing vial. Next, 0.390 mL *C. perfringens* was slowly loaded by pipette into the dosing vial to yield 1.5 μL *C. perfringens* and 33.5 μL PBS per injection. The dosing vial was gently rolled to mix, avoiding vigorous mixing to prevent aeration. Following mixing, the dosing vial was capped with a crimper.

Regarding treatment Group 3 (Oxyrase®+substrate+*C. perfringens*), 18.0 mL Oxyrase® oxygen scavenging membrane fragments was slowly loaded by pipette into a dosing vial. Next, 0.150 mL *C. perfringens* and 0.150 mL substrate were slowly loaded by pipette into the dosing vial to yield 1.5 μL *C. perfringens,* 1.5 μL substrate and 180 μL Oxyrase® oxygen scavenging membrane fragments per injection. The dosing vial was gently rolled to mix, avoiding vigorous mixing to prevent aeration. Following mixing, the dosing vial was capped with a crimper.

Regarding treatment Group 4 (*B. adolescentis* alone), 8.71 mL PBS was slowly loaded by pipette into a dosing vial. Next, 0.390 mL *B. adolescentis* was slowly loaded by pipette into the dosing vial to yield 1.5 μL *B. adolescentis* and 33.5 μL PBS per injection. The dosing vial was gently rolled to mix, avoiding vigorous mixing to prevent aeration. Following mixing, the dosing vial was capped with a crimper.

Regarding treatment Group 5 (Oxyrase®+substrate+*B. adolescentis*), 18.0 mL Oxyrase® oxygen scavenging membrane fragments was slowly loaded by pipette into a dosing vial. Next, 0.150 mL *B. adolescentis* and 0.150 mL substrate were slowly loaded by pipette into the dosing vial to yield 1.5 μL *B. adolescentis*, 1.5 μL substrate and 180 μL Oxyrase® oxygen scavenging membrane fragments per injection. The dosing vial was gently rolled to mix, avoiding vigorous mixing to prevent aeration. Following mixing, the dosing vial was capped with a crimper.

Doses to mice were administered within 30 minutes of receiving the test article from the microbiology laboratories using 27 G needles and Hamilton syringes according to the treatment and dosage schedule in Table 5 below.

TABLE 5

Groups and dosing schedule for 4T1 and LLC syngeneic mouse models

| Tumor Model | Group (n = 3) | Treatment |
|---|---|---|
| 4T1 | 1 | PBS (control) |
|  | 2 | *C. perfringens* |
|  | 3 | Oxyrase ® + substrate + *C. perfringens* |
|  | 4 | *B. adolescentis* |
|  | 5 | Oxyrase ® + substrate + *B. adolescentis* |
| LLC | 1 | PBS (control) |
|  | 2 | *C. perfringens* |
|  | 3 | Oxyrase ® + substrate + *C. perfringens* |
|  | 4 | *B. adolescentis* |
|  | 5 | Oxyrase ® + substrate + *B. adolescentis* |

On the day of treatment, each animal received one intra-tumor injection of anaerobe (*Clostridium perfringens* or *Bifidobacterium adolescentis*) alone or in combination with Oxyrase® oxygen scavenging membrane fragments and substrate as described in Table 5 above. Termination of the study or animals occurred at Day 29 post-inoculation or when tumor sizes exceeded 1,000 mm$^3$.

Study Log Study Director Animal Study Management Software (San Francisco, Calif.) was used to randomize animals. Data collection included body weights, tumor measurements, and daily clinical observations (e.g., morbidity, mortality, feeding, grooming). All data was analyzed using GraphPad InStat3 (GraphPad Software, Inc., La Jolla, Calif.). Treatment groups were compared with vehicle control groups using one-way ANOVA statistical analysis. If a significant difference ($p<0.05$) was observed, the Tukey-Kramer multiple comparison test was conducted.

Results

All results for tumor volume are reported in cubic millimeters (mm$^3$). All results for body weight are reported in grams (g).

Mouse 4T1 Breast Tumor Model

Animals were randomized on day 8 post-inoculation with a mean (±standard deviation) tumor size of: 136.61±43.35, 118.15±64.56, 174.55±108.43, 256.40±41.75, and 196.60±62.83 for Groups 1, 2, 3, 4 and 5 respectively. Mean body weights (±SD) at randomization were: 17.13±0.35, 16.77±0.51, 17.20±0.30, 17.20±0.10, and 17.07±0.15 for Groups 1, 2, 3, 4 and 5 respectively. Table 6 below summarizes the mean body weights (±SD) for the entire study. At termination day (Day 19), the mean tumor size (±SD) for the control group was 1872.22±1399.88 compared to 1508.71±1204.68, 1697.77±53.17, and 2359.78±418.19 for Groups 2, 3, and 4 respectively. Animals in Group 5 had to be terminated early (Day 8) due to tumor sizes exceeding humane limits. At termination, the mean body weight (±SD) for Group 5 was 1151±237.28.

TABLE 6

4T1 Murine Breast Cancer Model Mean Body Weights (±SD)

| | Day 1 | Day 4 | Day 6 | Day 8 | Day 13 | Day 15 | Day 19 |
|---|---|---|---|---|---|---|---|
| Group 1 | | | | | | | |
| 1 | 17.1 | 17.3 | 17.9 | 18.3 | 19.7 | 20.1 | 21.0 |
| 2 | 16.8 | 17.8 | 18.0 | 18.0 | 19.2 | 19.3 | 19.9 |
| 3 | 17.5 | 18.0 | 18.7 | 18.3 | 19.3 | 19.5 | 20.1 |
| Avg. | 17.13 | 17.70 | 18.20 | 18.20 | 19.40 | 19.63 | 20.33 |
| SD | 0.35 | 0.36 | 0.44 | 0.17 | 0.26 | 0.42 | 0.59 |
| Group 2 | | | | | | | |
| 4 | 16.2 | 16.7 | 17.4 | 17.7 | 19.0 | 19.9 | 19.8 |
| 5 | 17.2 | 17.6 | 18.6 | 19.0 | 20.0 | 19.9 | 21.1 |
| 6 | 16.9 | 17.3 | 18.5 | 18.3 | 19.2 | 18.9 | 19.5 |
| Avg. | 16.77 | 17.20 | 18.17 | 18.33 | 19.40 | 19.57 | 20.13 |
| SD | 0.51 | 0.46 | 0.67 | 0.65 | 0.53 | 0.58 | 0.85 |
| Group 3 | | | | | | | |
| 7 | 17.2 | | | | | | |
| 8 | 17.5 | 15.8 | 16.6 | 17.2 | 19.7 | 19.8 | 20.6 |
| 9 | 16.9 | 16.9 | 17.8 | 19.0 | 20.8 | 21.3 | 22. |
| Avg. | 17.20 | 16.35 | 17.20 | 18.10 | 20.25 | 20.55 | 21.30 |
| SD | 0.30 | 0.78 | 0.85 | 1.27 | 0.78 | 1.06 | 0.99 |
| Group 4 | | | | | | | |
| 10 | 17.2 | 17.7 | 19.2 | 19.4 | 20.2 | 20.4 | 20.5 |
| 11 | 17.1 | 16.8 | 17.5 | 18.0 | 19.3 | 19.6 | 20.0 |
| 12 | 17.3 | 16.5 | 17.9 | 18.1 | 14.4 | 19.4 | 20.0 |
| Avg. | 17.20 | 17.00 | 18.20 | 18.50 | 17.97 | 19.80 | 20.17 |
| SD | 0.10 | 0.62 | 0.89 | 0.78 | 3.12 | 0.53 | 0.29 |
| Group 5 | | | | | | | |
| 13 | 17.1 | 16.9 | 16.9 | 17.5 | Terminated | | |
| 14 | 17.2 | 15.3 | 16.0 | 16.3 | Terminated | | |
| 15 | 16.9 | 16.5 | 17.2 | 17.2 | Terminated | | |
| Avg. | 17.07 | 16.23 | 16.70 | 17.00 | Terminated | | |
| SD | 0.15 | 0.83 | 0.62 | 0.62 | Terminated | | |

Table 7 below summarizes the tumor volumes (±SD) for the entire study. Mean body weights (±SD) at termination were: 21.33±0.59, 20.13±0.85, 21.3±0.99, and 20.17±0.29 for Groups 1, 2, 3, and 4, respectively.

TABLE 7

4T1 Murine Breast Cancer Model Tumor Volumes (±SD)

| | Pre-Study (pre-inoculation) | Day 1 | Day 4 | Day 6 | Day 8 | Day 12 | Day 19 |
|---|---|---|---|---|---|---|---|
| Group 1 | | | | | | | |
| 1 | 36.95 | 98.56 | 280.87 | 371.77 | 644.14 | 1197.84 | 2001.85 |
| 2 | 67.19 | 127.48 | 222.00 | 117.39 | 174.76 | 250.79 | 412.04 |
| 3 | 83.70 | 183.80 | 347.34 | 351.15 | 670.72 | 735.64 | 3202.78 |
| Avg. | 62.61 | 136.61 | 283.40 | 280.10 | 496.54 | 728.09 | 1872.22 |
| SD | 23.71 | 43.35 | 62.71 | 141.29 | 278.99 | 473.57 | 1399.88 |
| Median | 67.2 | 127.5 | 280.9 | 351.2 | 644.14 | 735.64 | 2001.90 |
| Group 2 | | | | | | | |
| 4 | 39.54 | 77.84 | 192.69 | 273.62 | 291.52 | 476.58 | 819.64 |
| 5 | 77.80 | 192.61 | 548.02 | 647.38 | 784.46 | 1089.71 | 2899.73 |
| 6 | 22.12 | 84.01 | 130.09 | 202.55 | 224.49 | 369.66 | 809.61 |
| Avg. | 46.49 | 118.15 | 290.26 | 374.52 | 433.49 | 645.32 | 1509.66 |
| SD | 28.48 | 64.56 | 225.40 | 238.97 | 305.79 | 388.55 | 1203.85 |
| Median | 39.50 | 84.00 | 192.70 | 273.60 | 291.52 | 476.58 | 819.64 |
| Group 3 | | | | | | | |
| 7 | 45.96 | 75.89 | | | Deceased | | |
| 8 | 72.00 | 157.11 | 230.30 | 528.96 | 760.64 | 977.88 | 1389.08 |
| 9 | 49.40 | 290.64 | 359.85 | 574.99 | 419.90 | 1203.13 | 1735.37 |
| Avg. | 55.79 | 174.55 | 295.08 | 551.97 | 590.27 | 1090.51 | 1562.23 |
| SD | 14.15 | 108.43 | 91.60 | 32.55 | 240.94 | 159.28 | 244.86 |
| Median | 49.40 | 157.10 | 295.10 | 552.00 | 590.27 | 1090.50 | 1562.20 |
| Group 4 | | | | | | | |
| 10 | 96.07 | 287.16 | 530.59 | 759.75 | 891.67 | 1439.44 | 2020.06 |
| 11 | 68.42 | 273.16 | 283.02 | 521.83 | 658.01 | 1170.05 | 2232.43 |
| 12 | 33.14 | 208.88 | 393.25 | 542.97 | 844.95 | 1081.01 | 2826.84 |
| Avg. | 65.88 | 256.40 | 402.29 | 608.18 | 798.21 | 1230.17 | 2359.78 |
| SD | 31.55 | 41.75 | 124.03 | 131.69 | 123.64 | 186.62 | 418.19 |
| Median | 68.40 | 273.20 | 393.30 | 543.00 | 844.95 | 1170.10 | 2232.40 |
| Group 5 | | | | | | | |
| 13 | 72.54 | 169.52 | 690.74 | 1015.37 | 1424.33 | Terminated | |
| 14 | 60.81 | 151.84 | 226.32 | 317.71 | 995.59 | Terminated | |
| 15 | 150.08 | 268.43 | 564.31 | 773.85 | 1033.76 | Terminated | |
| Avg. | 94.48 | 196.60 | 493.79 | 702.31 | 1151.23 | Terminated | |
| SD | 48.51 | 62.83 | 240.10 | 354.29 | 237.28 | Terminated | |
| Median | 72.50 | 169.50 | 564.30 | 773.90 | 1033.80 | Terminated | |

Figure 3:
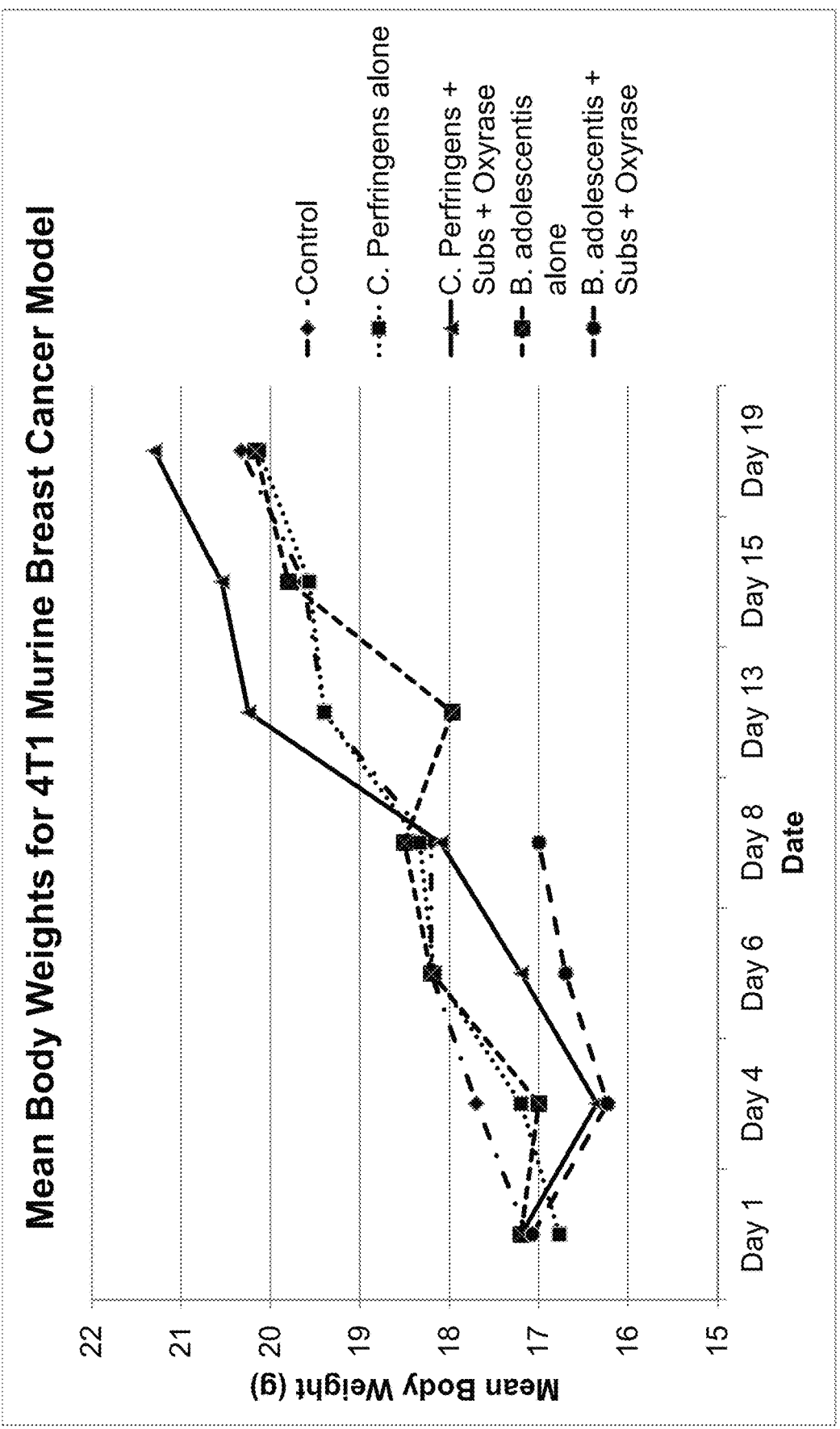
FIG. 3 is a graphical representation of the average body weights in grams ±standard deviation of mice inoculated with the 4T1 murine breast cancer cell line and treated with one of the following four compositions: PBS (control); *C. perfringens* alone; *C. perfringens*, substrate, and Oxyrase® oxygen scavenging membrane fragments; *B. adolescentis* alone; and *B. adolescentis*, substrate, and Oxyrase® oxygen scavenging membrane fragments. The dates correspond to days on which measurements were taken, with 11/5 corresponding to day of inoculation with one of the five treatments.
Figure 4:
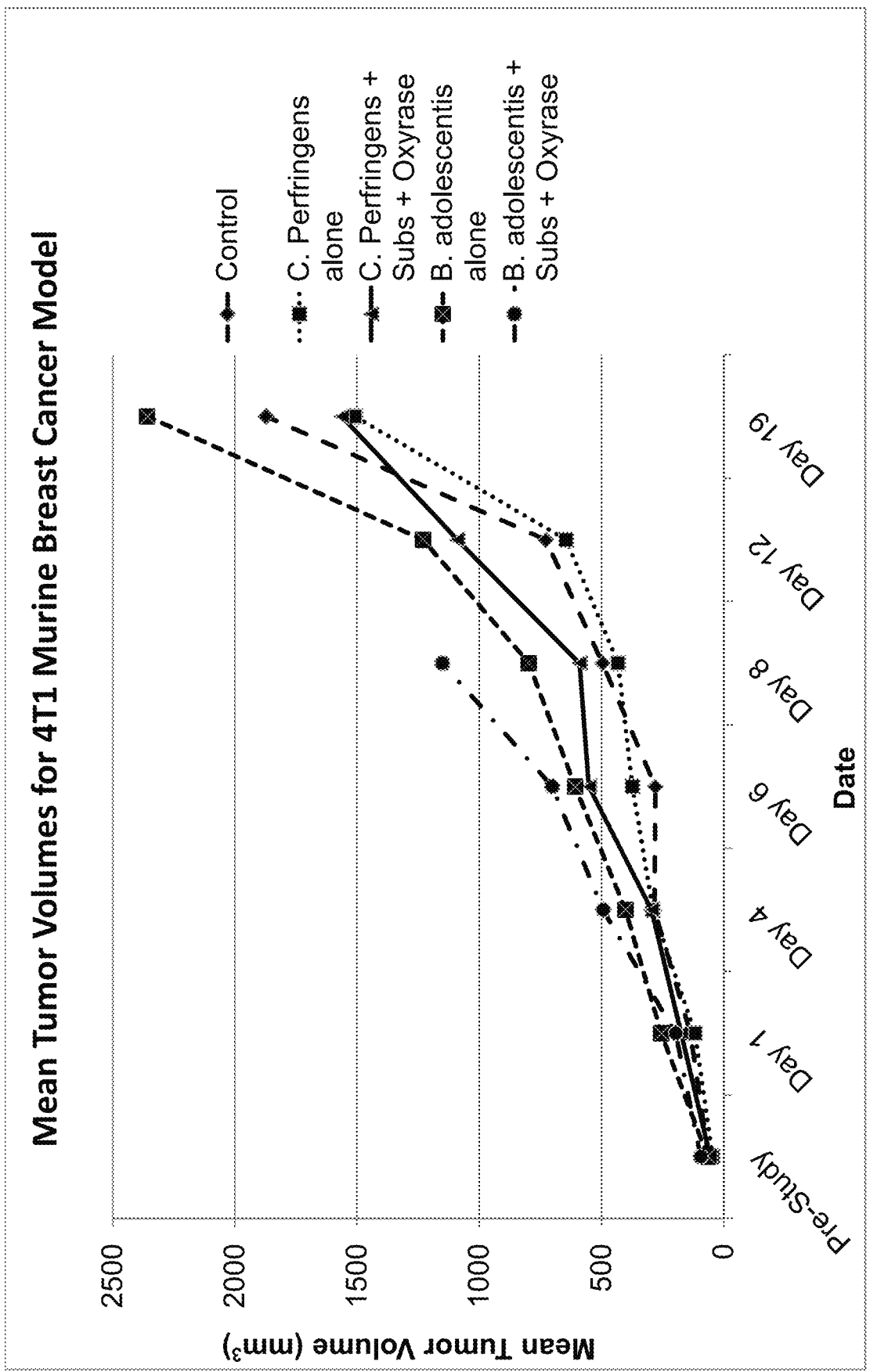
FIG. 4 is a graphical representation of the average tumor volume in $mm^3$ ±standard deviation of mice inoculated with the 4T1 murine breast cancer cell line and treated with one of the following: PBS (control); *C. perfringens* alone; *C. perfringens*, substrate, and Oxyrase® oxygen scavenging membrane fragments; *B. adolescentis* alone; and *B. adolescentis*, substrate, and Oxyrase® oxygen scavenging membrane fragments. The dates correspond to days on which measurements were taken, with 11/5 corresponding to day of inoculation with one of the five treatments.
Figure 5:
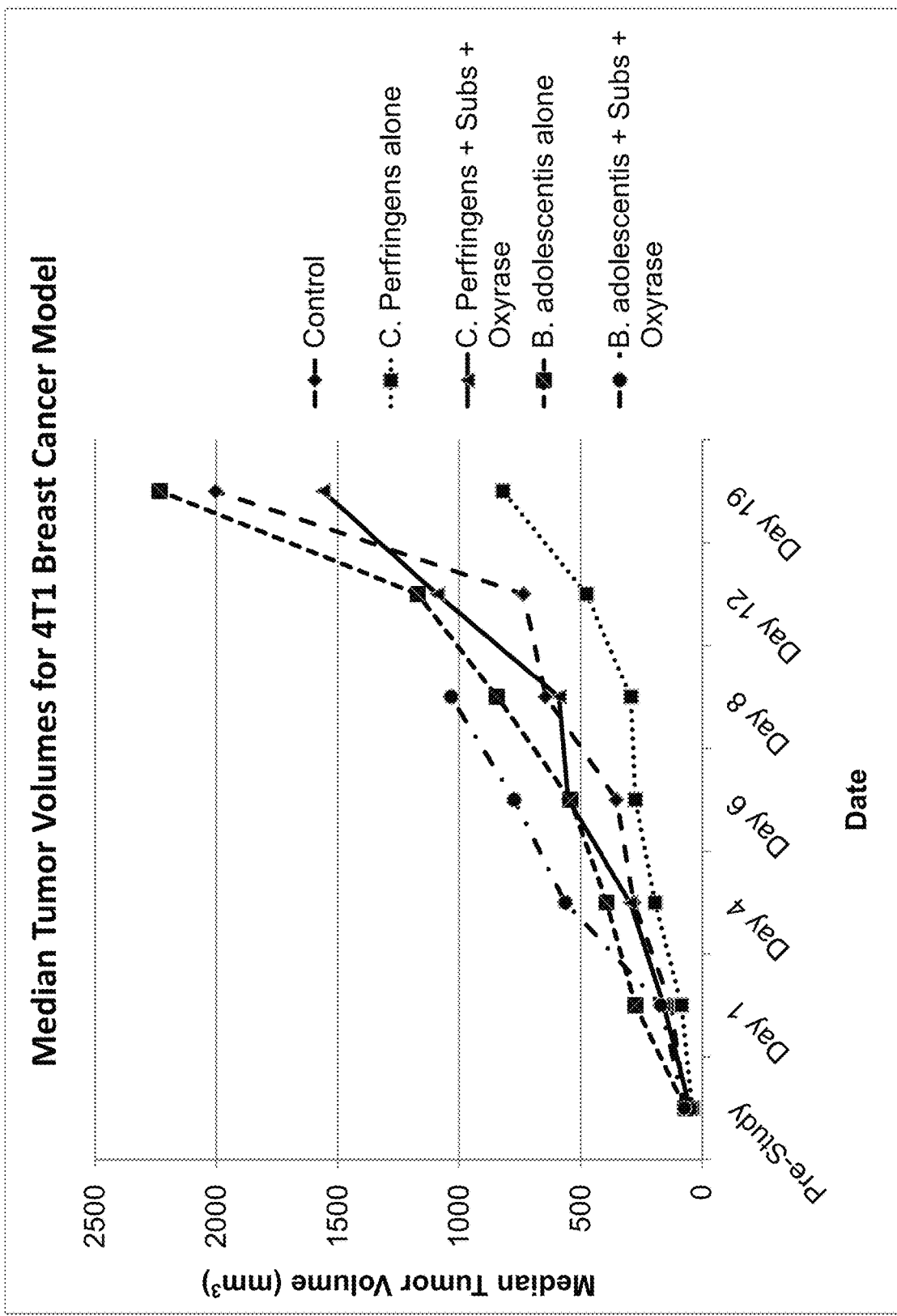
FIG. 5 is a graphical representation of the median tumor volume in $mm^3$ ±standard deviation of mice inoculated with the 4T1 murine breast cancer cell line and treated with one of the following: PBS (control); *C. perfringens* alone; *C. perfringens*, substrate, and Oxyrase® oxygen scavenging membrane fragments; *B. adolescentis* alone; and *B. adolescentis*, substrate, and Oxyrase® oxygen scavenging membrane fragments. The dates correspond to days on which measurements were taken, with 11/5 corresponding to day of inoculation with one of the five treatments.

FIG. 3 is a graphical illustration of the average body weights during the study period. On Day 2 post-treatment, there was a treatment-associated mortality in Group 3 (animal 7). All surviving animals in Group 3 and animals in Group 5 showed clinical signs including rough coats and hypoactivity following test article administration. FIG. 4 is a graphical illustration of mean tumor volume, while FIG. 5 is a graphical illustration of median tumor volume.

Mouse LLC Lung Cancer Model

Animals were randomized on day 8 post-inoculation with a mean (±SD) tumor size of: 169.29±40.07, 197.36±79.03, 206.56±47.49, 187.30±24.70, and 172.39±18.72 for Groups 1, 2, 3, 4, and 5 respectively. Mean body weights (±SD) at randomization were 17.23±0.23, 17.30±0.26, 17.47±0.06, 17.43±0.42, and 17.30±0.26 for Groups 1, 2, 3, 4, and 5 respectively. Table 8 below summarizes the mean body weights (±SD) for the entire study. At day of termination (Day 11), the mean tumor size (±SD) for the control group was 1243.07±314.28 compared to 1593.0±305.42, 206.56±47.49, 1280.46±215.15, and 1285.76±291.85 for Groups 2, 3, 4, and 5 respectively.

TABLE 8

LLC Murine Lung Cancer Model Mean Body Weights (±SD)

| | Day 1 | Day 4 | Day 6 | Day 8 |
|---|---|---|---|---|
| Group 1 | | | | |
| 1 | 17.1 | 17.4 | 18.8 | 18.6 |
| 2 | 17.1 | 18.0 | 18.2 | 17.3 |
| 3 | 17.5 | 19.4 | 20.4 | 20.0 |
| Avg. | 17.23 | 18.27 | 19.13 | 18.63 |
| SD | 0.23 | 1.03 | 1.14 | 1.35 |
| Group 2 | | | | |
| 4 | 17.2 | 17.9 | 18.9 | 19.2 |
| 5 | 17.6 | 19.7 | 20.5 | 21.0 |
| 6 | 17.1 | 17.3 | 18.2 | 16.6 |
| Avg. | 17.30 | 18.30 | 19.20 | 18.93 |
| SD | 0.26 | 1.25 | 1.18 | 2.21 |
| Group 3 | | | | |
| 7 | 17.5 | | Terminated | |
| 8 | 17.4 | | Terminated | |
| 9 | 17.5 | 13.2 | | Terminated |
| Avg. | 17.47 | 13.2 | | Terminated |
| SD | 0.06 | 0 | | Terminated |
| Group 4 | | | | |
| 10 | 17.9 | 18.6 | 18.8 | 19.6 |
| 11 | 17.1 | 17.6 | 18.4 | 19.0 |

TABLE 8-continued

LLC Murine Lung Cancer Model Mean Body Weights (±SD)

|  | Day 1 | Day 4 | Day 6 | Day 8 |
|---|---|---|---|---|
| 12 | 17.3 | 18.0 | 17.6 | 16.5 |
| Avg. | 17.43 | 18.07 | 18.27 | 18.37 |
| SD | 0.42 | 0.50 | 0.61 | 1.64 |
| Group 5 |  |  |  |  |
| 13 | 17.9 | 17.2 | 19.2 | 17.9 |
| 14 | 17.8 | 17.0 | 19.5 | 17.8 |
| 15 | 19.0 | 18.4 | 20.5 | 19.0 |
| Avg. | 18.23 | 17.53 | 19.73 | 18.23 |
| SD | 0.67 | 0.76 | 0.68 | 0.67 |

Table 9 below summarizes the tumor volumes (±SD) for the entire study. Mean body weights (±SD) at termination were: 18.63±1.35, 18.93±2.21, 18.37±1.64, and 19.73±0.68 for Groups 1, 2, 4, and 5 respectively. All animals in Group 3 died by Day 4 following administration of the test article.

TABLE 9

LLC Murine Lung Cancer Model Tumor Volumes (±SD)

|  | Pre-Study (pre-inoculation) | Day 1 | Day 4 | Day 6 | Day 8 |
|---|---|---|---|---|---|
| Group 1 |  |  |  |  |  |
| 1 | 14.24 | 153.73 | 331.91 | 535.56 | 912.24 |
| 2 | 32.33 | 214.81 | 584.67 | 471.54 | 1279.31 |
| 3 | 59.33 | 139.34 | 473.68 | 679.81 | 1537.65 |
| Avg. | 35.30 | 169.29 | 463.42 | 562.30 | 1243.07 |
| SD | 22.69 | 40.07 | 126.69 | 106.68 | 314.28 |
| Median | 32.30 | 153.73 | 473.68 | 535.56 | 1279.30 |
| Group 2 |  |  |  |  |  |
| 4 | 32.25 | 111.81 | 279.51 | 495.74 | 1397.70 |
| 5 | 26.14 | 212.63 | 191.72 | 493.23 | 1436.34 |
| 6 | 33.96 | 267.64 | 931.43 | 894.34 | 1944.96 |
| Avg. | 30.78 | 197.36 | 467.55 | 627.77 | 1593.00 |
| SD | 4.11 | 79.03 | 404.12 | 230.86 | 305.42 |
| Median | 32.35 | 212.63 | 279.51 | 495.74 | 1436.30 |
| Group 3 |  |  |  |  |  |
| 7 | 60.85 | 176.73 | Terminated |  |  |
| 8 | 127.74 | 261.32 | Terminated |  |  |
| 9 | 14.72 | 181.62 | 305.32 | Terminated |  |
| Avg. | 67.77 | 206.56 | 305.32 | Terminated |  |
| SD | 56.83 | 47.49 | 0.00 | Terminated |  |
| Median | 60.85 | 181.62 | 305.32 | Terminated |  |
| Group 4 |  |  |  |  |  |
| 10 | 0.00 | 215.10 | 433.79 | 736.46 | 1482.22 |
| 11 | 51.25 | 178.90 | 253.76 | 934.53 | 1054.04 |
| 12 | 48.22 | 167.90 | 707.37 | 637.53 | 1305.12 |
| Avg. | 33.16 | 187.30 | 464.98 | 769.51 | 1280.46 |
| SD | 28.75 | 24.70 | 228.41 | 151.23 | 215.15 |
| Median | 48.22 | 178.90 | 433.79 | 736.46 | 1305.10 |
| Group 5 |  |  |  |  |  |
| 13 | 48.34 | 152.22 | 357.31 | 531.79 | 1502.00 |
| 14 | 50.59 | 189.28 | 363.13 | 702.81 | 953.66 |
| 15 | 35.33 | 175.68 | 610.45 | 1072.45 | 1401.62 |
| Avg. | 44.75 | 172.39 | 443.63 | 769.02 | 1285.76 |
| SD | 8.24 | 18.75 | 144.50 | 276.34 | 291.95 |
| Median | 48.34 | 175.68 | 363.13 | 702.81 | 1401.60 |

Figure 6:
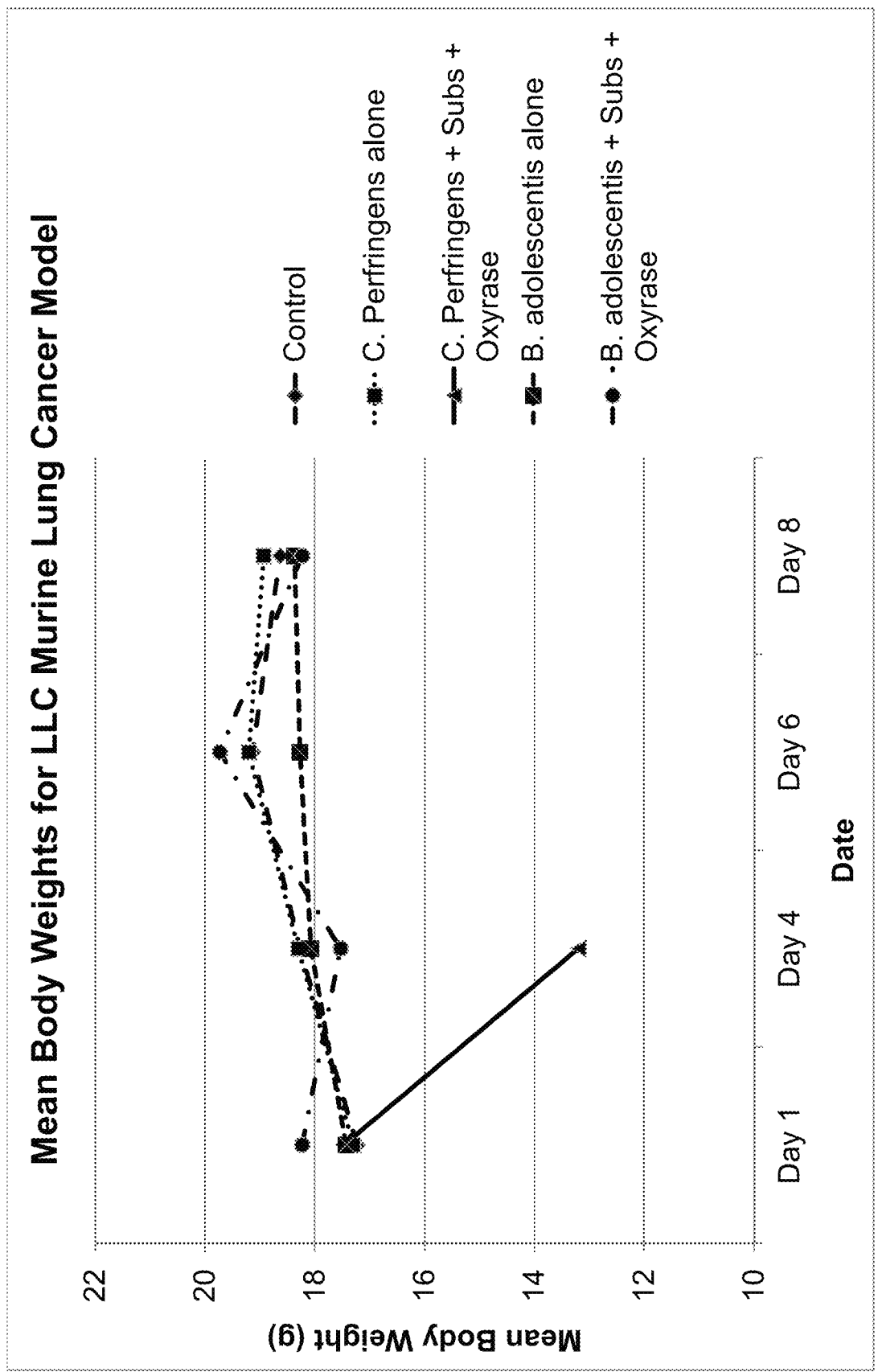
FIG. 6 is a graphical representation of the average body weights in grams ±standard deviation of mice inoculated with the LLC murine lung cancer cell line and treated with one of the following: PBS (control); *C. perfringens* alone; *C. perfringens*, substrate, and Oxyrase® oxygen scavenging membrane fragments; *B. adolescentis* alone; and *B. adolescentis*, substrate, and Oxyrase® oxygen scavenging membrane fragments. The dates correspond to days on which measurements were taken, with 11/5 corresponding to day of inoculation with one of the five treatments.
Figure 7:
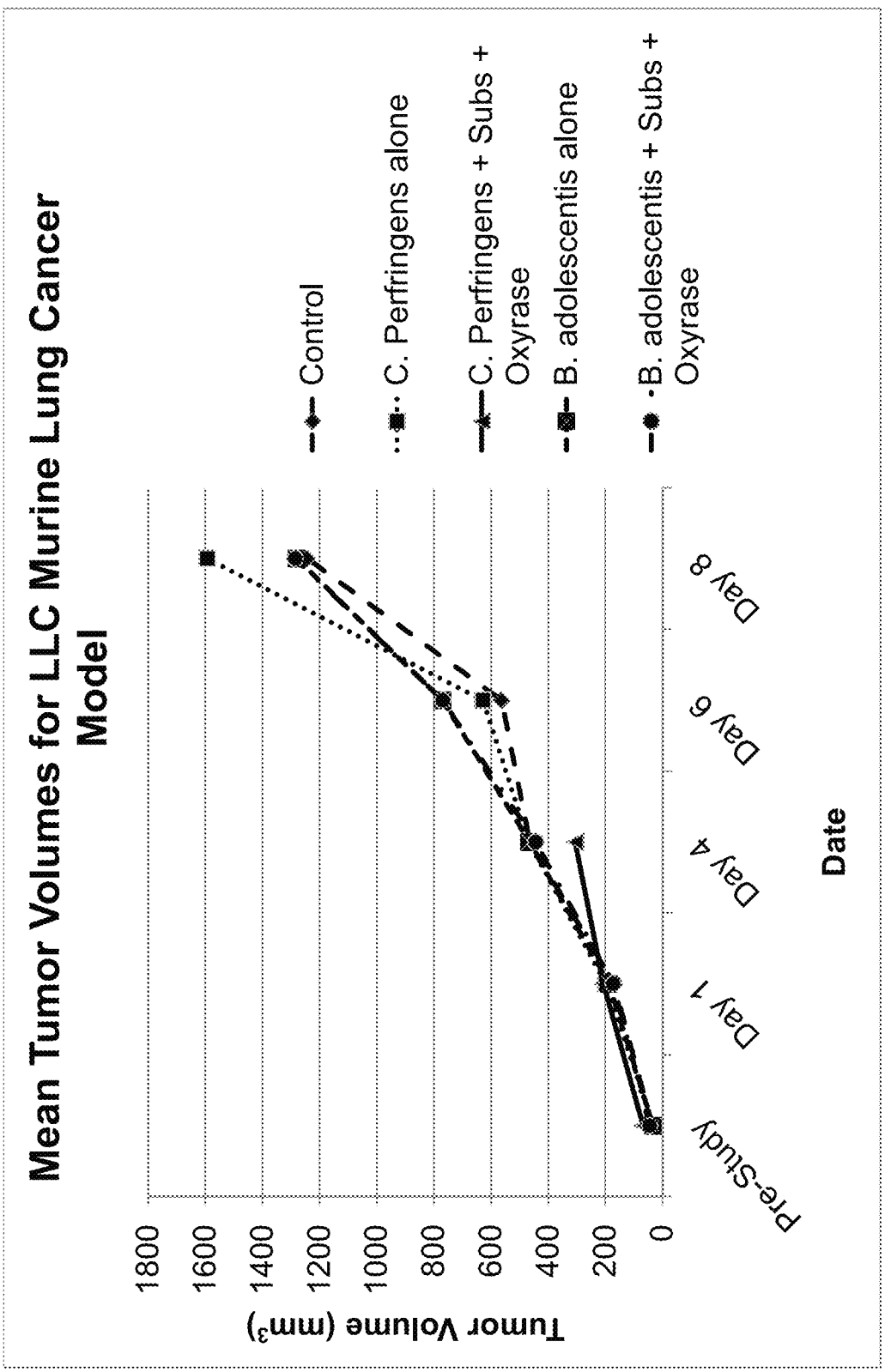
FIG. 7 is a graphical representation of the average tumor volume in $mm^3$ ±standard deviation of mice inoculated with the LLC murine lung cancer cell line and treated with one of the following: PBS (control); *C. perfringens* alone; *C. perfringens*, substrate, and Oxyrase® oxygen scavenging membrane fragments; *B. adolescentis* alone; and *B. adolescentis*, substrate, and Oxyrase® oxygen scavenging membrane fragments. The dates correspond to days on which measurements were taken, with 11/5 corresponding to day of inoculation with one of the five treatments.
Figure 8:
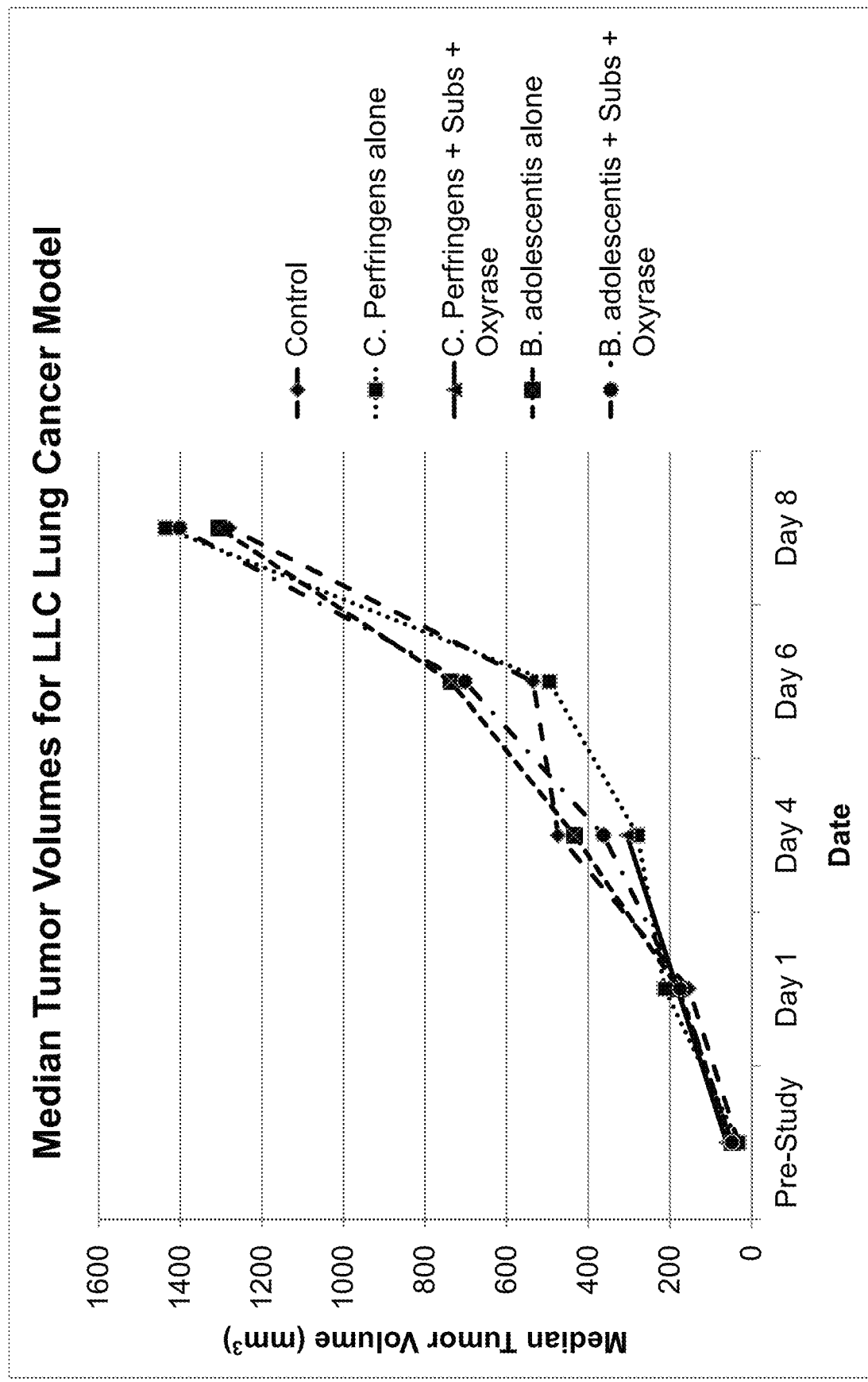
FIG. 8 is a graphical representation of the median tumor volume in $mm^3$ ±standard deviation of mice inoculated with the LLC murine lung cancer cell line and treated with one of the following: PBS (control); *C. perfringens* alone; *C. perfringens*, substrate, and Oxyrase® oxygen scavenging membrane fragments; *B. adolescentis* alone; and *B. adolescentis*, substrate, and Oxyrase® oxygen scavenging membrane fragments. The dates correspond to days on which measurements were taken, with 11/5 corresponding to day of inoculation with one of the five treatments.

FIG. 6 is a graphical illustration of the average body weights for the study period. FIG. 7 is a graphical illustration of the mean tumor volumes for the study period, while FIG. 8 is a graphical illustration of the median tumor volumes for the study period.

DISCUSSION

As shown in Tables 1-4 above, suspensions containing Oxyrase® oxygen scavenging membrane fragments succeeded in preserving and storing biological specimens under typical freezing conditions for a prolonged period of time. The consistent recovery of specimens after being maintained at sub-zero temperatures has been achieved by using high concentrations of cryoprotectants to lower the freezing point of the mixture used to preserve the cells. For example, if glycerol were used in a medium at 53% by weight, then the freezing temperature decreases to −26 degrees Celsius. A standard freezer operates at −20 degrees Celsius.

Here a panel of microorganisms in a medium containing 53% glycerol has been stored for a period of 15 months in a standard freezer. The medium did not freeze, and high numbers of viable cells were recovered from the preserved cells. The microbial cells were not adversely affected by the high concentration of glycerol.

Some of the anaerobe microbes tested are the most difficult of microbes to isolate, grow and preserve, particularly *F. nucleatum, P. levii,* and *P. melaninogenica*. It should be noted that the recovery scores remained consistent through the storage period with the exception of these challenging microbes. Sampling these microbes is problematic, as they are difficult to suspend uniformly. Every effort was made to keep the sampling time as short as possible so as to not lose viability due to exposure to ambient air. These sampling problems can particularly be seen across the *F. nucleatum* samples. Note some of the values drop to zero, or no growth, as indicated by "NG" and then a positive value is obtained on the next sample. This reflects the difficulty in obtaining uniform samples rather than a loss in viability.

Some of this variability can be overcome by using a different or improved technique. For example, if sterile oil is overlaid onto the suspension liquid containing Oxyrase® oxygen scavenging membrane fragments and a microbe in the vial, subsequent samples become more stable and consistent in numbers recovered. This is shown in the rows of Tables 1 and 2 corresponding to *F. nucleatum* with oil and *P. melaninogenica* with oil. The greater stability and consistency is due to the oil blocking air (and subsequently oxygen) from dissolving into the underlying suspension, thereby protecting the stored microbe from the deleterious effect of oxygen.

Unlike other storage methods, such as lyophilization, the majority of microbes that went into storage using the Oxyrase® suspension were recovered (>>1:100). Other storage methods have exhibited recovery of anaerobes at the level of one in a million or less.

The superior recovery of cells stored in the Oxyrase® suspension is due to the cells not freezing. The cryoprotectant, in the first case glycerol, is neither toxic nor harmful to the microbes. Not only are the microbes spared the detrimental effects of freezing and thawing, but they are also always kept at sub-zero temperatures, which contributes to the stability of the stored samples.

As mentioned above, FIG. 2 shows the temperature ranges through which the storage freezer cycled. However, despite the fluctuation in temperature, the data in Tables 1 and 2 show that the viability of the stored microbes is relatively constant, even taking into account sampling issues. During storage, cells were always at sub-zero temperatures, and at these temperatures, the cells were in a static state, which contributed to the storage stability of the cells.

As stated above, PEG400 is impermeable to the cell membrane. However, despite its limited action to the outside of a cell, the cell and its contents reside at subzero temperatures in suspension. The results of the second experiment thereby support the interpretation that cell contents do not freeze at these temperatures. Damage due to freezing and thawing, when it occurs, must take place outside the membrane.

The contents inside a cell are very different from the solutes and solutions encountered in a laboratory. For example, the DNA chromosome of a representative microbe such as *E. coli* is millions of base pairs long and is greater than $1 \times 10^9$ daltons in mass. Often a cell contains two such molecules. These molecules, in addition to transfer RNAs, ribosomes, and proteins, are contained in a compartment 3-5 µm in length and 2-3 µm in diameter. It would not be surprising to find that the contents of microbial cells do not freeze at typical freezer temperatures.

Further, experimental results as shown in Tables 5-9 and FIGS. 3-8 suggest that Oxyrase® oxygen scavenging membrane fragments, when used in conjunction with anaerobes, may suppress tumor growths. Only tumors infected with both anaerobes and Oxyrase® oxygen scavenging membrane fragments exhibited changes in growth. Tumors infected with only anaerobes were not affected. This is most likely due to Oxyrase® oxygen scavenging membrane fragments improving anaerobe infection of tumors.

It should be noted that anaerobes differed in their effects on tumors. For example, *C. perfringens* is a vigorous pathogen known to cause gas gangrene. When used in the third set of experiments, it killed not only the tumor but also the host animal. *B. adolescentis* is not a pathogen and is commonly used in yogurt. However, upon infection of tumors with Oxyrase® oxygen scavenging membrane fragments, *B. adolescentis* only affected breast tumors, which exhibited excessive growth. Therefore, animals infected with anaerobes alone did not exhibit altered tumor growth. These results indicate that there is an opportunity to use a wide range of either available or genetically engineered anaerobes to infect and treat tumors particularly when used with the directed administration of Oxyrase® oxygen scavenging membrane fragments.

Storing suspensions in a liquid state makes working with them easier and simpler, as samples can quickly and simply be removed from a vial. For more difficult anaerobes, the liquid suspensions make possible maintenance and storage, which translates into higher inefficiencies and lower costs.

Being able to maintain stored cells in a self-defrosting freezer contributes to reduced effort needed to maintain the pharmaceutical compositions. Costs are kept to a minimum when multiple freezers are used, and savings result from the lower labor cost in maintaining freezers and not having to defrost them. In addition to reduced labor costs that result from storage of pharmaceutical compositions containing Oxyrase® oxygen scavenging membrane fragments, the costs for the equipment are substantially reduced, as standard household freezers are thousands of dollars cheaper than the costs of cryofreezers. Therefore, the application significantly reduces the cost and labor associated with preserving these compositions.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

The invention claimed is:

1. A method for treating a patient with a tumor, comprising intratumorally administering to the patient a therapeutic composition comprising a pharmaceutically effective amount of oxygen scavenging membrane fragments, a pharmaceutically effective amount of anaerobe bacteria, and a cryoprotectant;
wherein the oxygen scavenging membrane fragments are derived from the cytoplasmic membranes of *Escherichia, Salmonella, Gluconobacter, Pseudomonas*, or *Acetobacter*; and
wherein the anaerobe bacteria is *Bacteroides, Bifidobacterium, Clostridium, Fusobacterium, Porphyromonas, Peptostreptococcus, Prevotella*, or a combination thereof.

2. The method of claim 1, wherein the cryoprotectant is glycerol or polyethylene glycol.

3. The method of claim 1, wherein the therapeutic composition contains from about 15 wt % to about 65 wt % of the cryoprotectant.

4. The method of claim 1, wherein the oxygen scavenging membrane fragments are derived from the cytoplasmic membranes of *Escherichia coli, Salmonella typhimurium, Gluconobacter oxydans, Pseudomonas aeruginosa*, or *Acetobacter*.

5. The method of claim 1, wherein the therapeutic composition further comprises a hydrogen donating substance which is an acid or a salt thereof.

6. The method of claim 1, wherein the therapeutic composition is in the form of an injection, solution, suspension, or emulsion.

7. The method of claim 1, wherein the therapeutic composition contains the oxygen scavenging membrane fragments in an amount greater than 0.01 units per milliliter.

8. The method of claim 1, wherein the tumor is a breast, cervical, colon, liver, lung, ovarian, pancreatic, prostate, brain, or bone cancer tumor.

9. The method of claim 1, wherein the therapeutic composition is administered in combination with chemotherapy, immunotherapy, radiation therapy, drug therapy, or cell transplantation.

10. The method of claim 1, wherein the anaerobe bacteria are present in the therapeutic composition in an amount of about $1 \times 10^6$ to about $1 \times 10^8$ CFU/mL.

11. The method of claim 1, wherein the anaerobe bacteria is *Bacteroides fragilis, Bifidobacterium adolescentis, Clostridium perfringens, Fusobacterium nucleatum, Porphyromonas levii, Peptostreptococcus anaerobius, Prevotella melaninogenica*, or a combination thereof.

12. The method of claim 1, further comprising intratumorally administering a priming composition comprising oxygen scavenging membrane fragments derived from the cytoplasmic membranes of *Escherichia, Salmonella, Gluconobacter, Pseudomonas*, or *Acetobacter* prior to intratumorally administering the therapeutic composition.

13. The method of claim 1, wherein the therapeutic composition contains the oxygen scavenging membrane fragments in an amount greater than 0.5 units per milliliter.

14. The method of claim 1, wherein the therapeutic composition contains the oxygen scavenging membrane fragments in an amount greater than 1 unit per milliliter.

15. The method of claim 1, wherein the therapeutic composition contains the oxygen scavenging membrane fragments in an amount of from 1 unit per milliliter to 10 units per milliliter.

16. The method of claim 1, wherein the therapeutic composition contains the oxygen scavenging membrane fragments in an amount of from 5 units per milliliter to 10 units per milliliter.

* * * * *